US012090089B2

(12) United States Patent
Patel et al.

(10) Patent No.: US 12,090,089 B2
(45) Date of Patent: Sep. 17, 2024

(54) LIGHTING ATTACHMENT FOR WELDING HELMETS

(71) Applicant: Illinois Tool Works Inc., Glenview, IL (US)

(72) Inventors: Nishank Patel, Appleton, WI (US); Eric Sommers, Appleton, WI (US); John Gabriel Touzinsky, Kimberly, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 121 days.

(21) Appl. No.: 15/813,857

(22) Filed: Nov. 15, 2017

(65) Prior Publication Data

US 2018/0133060 A1    May 17, 2018

Related U.S. Application Data

(60) Provisional application No. 62/544,484, filed on Aug. 11, 2017, provisional application No. 62/423,134, filed on Nov. 16, 2016.

(51) Int. Cl.
*A61F 9/06* (2006.01)
*A42B 3/04* (2006.01)
*A42B 3/22* (2006.01)
*F21L 4/08* (2006.01)
*F21V 9/08* (2018.01)
*F21V 15/01* (2006.01)
*F21V 21/088* (2006.01)
*F21V 23/04* (2006.01)
*F21Y 115/10* (2016.01)

(52) U.S. Cl.
CPC .............. *A61F 9/06* (2013.01); *A42B 3/0406* (2013.01); *A42B 3/0446* (2013.01); *A42B 3/225* (2013.01); *F21L 4/08* (2013.01); *F21V 9/08* (2013.01); *F21V 15/01* (2013.01); *F21V 21/088* (2013.01); *F21V 23/0464* (2013.01); *A61F 9/065* (2013.01); *F21Y 2115/10* (2016.08)

(58) Field of Classification Search
CPC ....... A42B 3/0406; A42B 3/0446; A61F 9/06; F12L 4/08; F12L 9/08; F12L 15/01; F12L 21/088; F12L 23/0464
See application file for complete search history.

(56) References Cited

U.S. PATENT DOCUMENTS

| | | | | |
|---|---|---|---|---|
| 4,283,798 A * | 8/1981 | Kuehn | .................... | G01C 15/14 33/366.26 |
| 6,113,243 A * | 9/2000 | Saul | ..................... | A42B 3/0453 362/802 |
| 6,244,721 B1 * | 6/2001 | Rodriguez | ............. | A42B 3/044 362/183 |
| 6,340,234 B1 * | 1/2002 | Brown, Jr. | ................ | A61F 9/06 362/105 |
| 6,966,668 B2 * | 11/2005 | Cugini | ................... | H05B 45/22 362/249.05 |
| 7,161,116 B2 * | 1/2007 | Steinemann | ............. | A61F 9/06 2/8.2 |

(Continued)

*Primary Examiner* — Richale L Quinn
(74) *Attorney, Agent, or Firm* — McAndrews, Held & Malloy, Ltd.

(57) ABSTRACT

A welding-type helmet includes a cover with a channel recessed from an external surface of the cover, the channel being configured to house a removable light source within the channel.

9 Claims, 12 Drawing Sheets

(56) References Cited

U.S. PATENT DOCUMENTS

| | | | | |
|---|---|---|---|---|
| 7,178,932 B1* | 2/2007 | Buckman | | A61F 9/068 |
| | | | | 362/373 |
| 7,520,630 B2* | 4/2009 | Murphy | | A62B 18/08 |
| | | | | 362/105 |
| 7,534,005 B1 | 5/2009 | Buckman | | |
| 7,934,846 B1* | 5/2011 | Schwanz | | A61F 9/06 |
| | | | | 362/106 |
| 8,550,651 B2* | 10/2013 | Waters | | F21L 4/027 |
| | | | | 362/249.02 |
| 9,073,138 B2* | 7/2015 | Wills | | A42B 3/042 |
| 9,526,287 B2* | 12/2016 | Waters | | A42B 1/244 |
| 9,609,902 B2* | 4/2017 | Waters | | A42B 1/244 |
| 9,872,530 B2* | 1/2018 | Waters | | F21V 5/04 |
| 10,159,294 B2* | 12/2018 | Waters | | A42B 1/242 |
| 10,251,787 B2* | 4/2019 | Currie | | A61F 9/067 |
| 2005/0077278 A1* | 4/2005 | Steinemann | | A61F 9/06 |
| | | | | 219/147 |
| 2008/0158502 A1 | 7/2008 | Becker et al. | | |
| 2010/0007938 A1* | 1/2010 | Huh | | G01J 1/0219 |
| | | | | 340/870.07 |
| 2011/0101890 A1* | 5/2011 | Robinson | | F21K 9/20 |
| | | | | 315/320 |
| 2013/0214701 A1* | 8/2013 | Forgey, II | | G09G 3/16 |
| | | | | 315/307 |
| 2013/0271602 A1* | 10/2013 | Bentley | | G06T 7/215 |
| | | | | 348/143 |
| 2014/0111977 A1* | 4/2014 | Nyberg | | A42B 3/0446 |
| | | | | 362/105 |
| 2015/0061874 A1* | 3/2015 | Kim | | A42B 3/285 |
| | | | | 362/106 |
| 2015/0327615 A1* | 11/2015 | Gelb | | F21L 4/08 |
| | | | | 362/105 |
| 2016/0163221 A1 | 6/2016 | Sommers et al. | | |
| 2016/0260261 A1 | 9/2016 | Hsu | | |
| 2018/0055131 A1* | 3/2018 | Thompson | | A42B 3/061 |
| 2018/0064199 A1* | 3/2018 | Battis | | A42B 3/283 |
| 2018/0071854 A1* | 3/2018 | Matthews | | H04N 5/33 |
| 2019/0053562 A1* | 2/2019 | Bailey | | A42B 3/0453 |

* cited by examiner

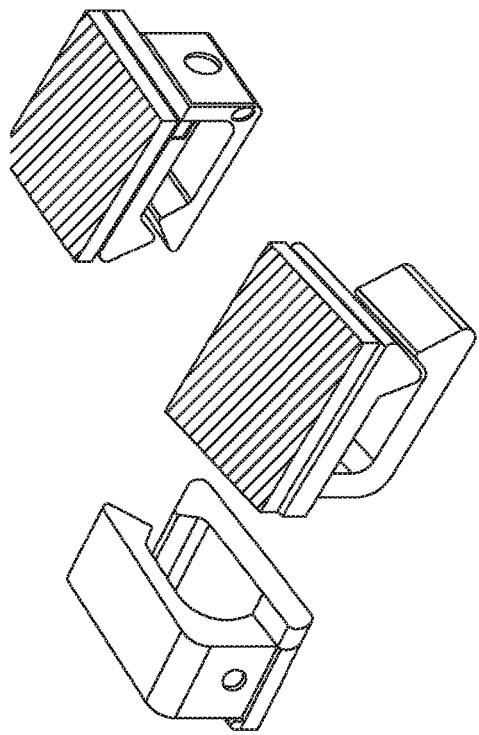
FIG. 8
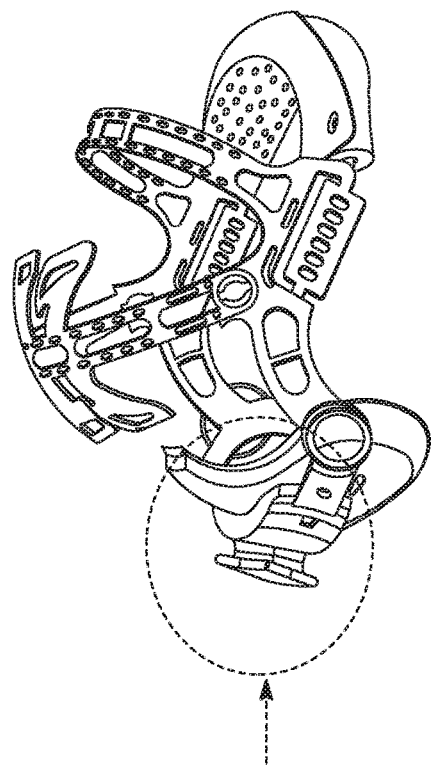
FIG. 9
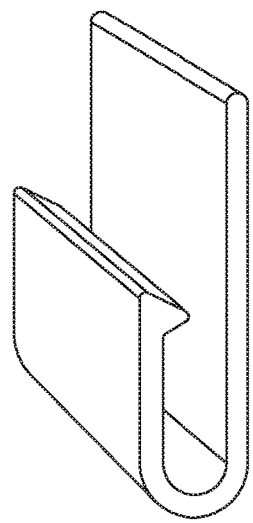
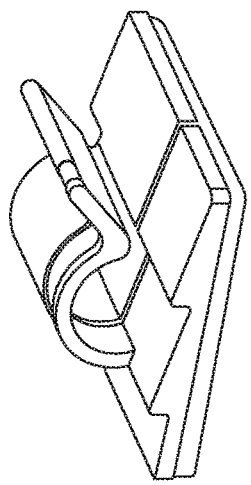

LIGHTING ATTACHMENT FOR WELDING HELMETS

CROSS-REFERENCE TO RELATED APPLICATIONS

This patent application claims priority to and the benefit of U.S. Provisional Patent Application Ser. No. 62/423,134, filed on Nov. 16, 2016, and U.S. Provisional Patent Application Ser. No. 62/544,484, filed on Aug. 11, 2017, both of which are incorporated herein by reference in their entirety.

BACKGROUND

Welding helmets are an important personal protection device for weld operators. Conventional welding helmets have a pivoting face shield that can be lifted up and down to improve visibility, while staying on the head of the wearer. Some weld operators prefer to keep their face shields down in between welds to maintain safety. However, some welding helmets have an auto-darkening feature in the lens, with a minimum darkness shade that often prevents operators from viewing a workpiece when a welding arc is not being generated. In order to improve visibility when light from the arc is not illuminating the operator's field of view, the operator may raise the face shield, which compromises safety of the welder. A solution that allows the operator to maintain the face shield in a protective position, while improving visibility, is therefore desirable.

SUMMARY

Welding helmets that include attachments for light sources to improve weld operator visibility and convenience are disclosed, substantially as illustrated by and described in connection with at least one of the figures, as set forth more completely in the claims.

BRIEF DESCRIPTION OF THE DRAWINGS

FIG. 8 illustrates example lighting attachment mechanisms for the light source(s), in accordance with aspects of this disclosure.

FIG. 9 illustrates an example lighting attachment mechanisms and potential location for the light source(s) on a helmet frame, in accordance with aspects of this disclosure.

The figures are not necessarily to scale. Similar or identical reference numerals may be used to refer to similar or identical components.

DETAILED DESCRIPTION

Figure 1:
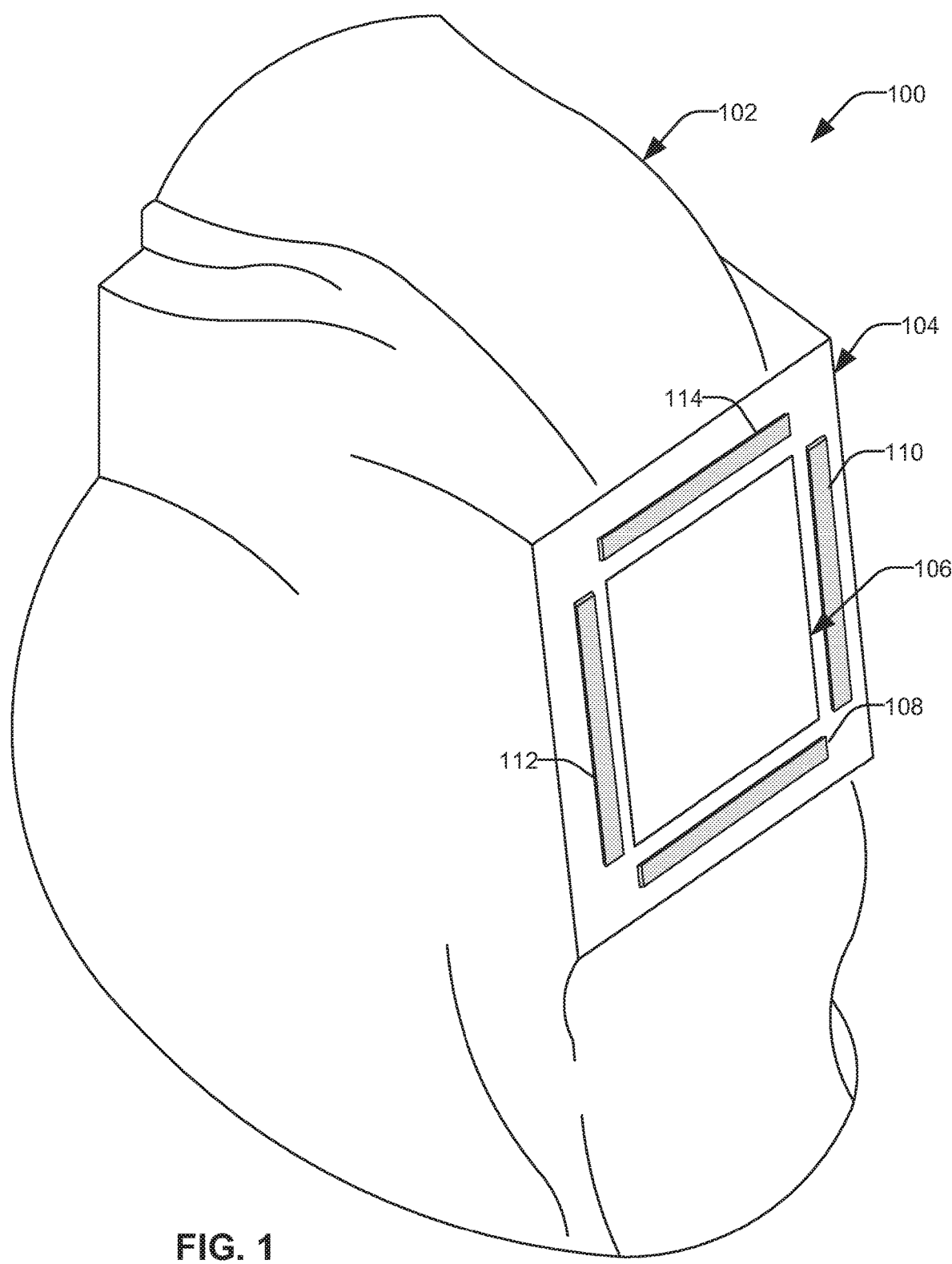
FIG. 1 illustrates an example welding helmet including a lens retaining bezel having a channel, in accordance with aspects of this disclosure.

The present disclosure provides a welding helmet that includes attachments for one or more light source(s). In particular, the helmet assembly is configured to integrate a light source on a surface of the helmet that is resistant to the hazards of a welding environment. Disclosed examples also provide easily replaceable components, which allow existing helmets to be retrofitted with the light source(s) and/or attachment mechanisms.

Conventional helmets provide weld operators with adequate lighting to keep their welding helmets down between welds include using small flashlights. However, such conventional solutions have limitations in positioning, are bulky and/or heavy, and do not provide a sufficiently wide field of light at the work area or sufficient brightness. Disclosed example welding helmets include lights incorporated therein, configured to illuminate a work area in an operators field of view. For example, a retaining bezel of a front cover lens on a welding helmet may include integrated and/or attached light source(s). The retaining bezel is an easily replaceable component of the helmet and is often in close proximity to the workpiece.

Helmets used in welding situations commonly employ auto darkening filter (ADF) lenses, which provides eye protection from the intense light generated by a welding arc. ADF lenses can use layers of polarizers and liquid crystals (see, e.g., FIG. 10) to filter out varying amounts of light based on electric input (e.g., light sensors, photodiodes, etc.). In an inactive state, such an ADF lens may be set between a shade 3.0-5.0, as defined by standards such as ANSI Z87.1 (i.e. similar to a tinted sunglass lens). When a welder strikes an arc, the lens automatically darkens to a shade range between 8.0-13.0 to protect the welder's eyes from the intense light generated by the arc.

For example, the inactive state is used during non-welding activities, such as grinding and welding setup. Depending on environmental lighting, welders might have difficulty seeing through the heavily tinted lens, which can prompt the welding to lift the retaining bezel and/or helmet to get an unfiltered view of the workspace. This action results in reduced protection against safety hazards, lowers productivity (i.e. from repeatedly flipping the helmet up and down), and also places strain on the welder's neck from the repetitive movement.

In some environments, the workspace is so poorly illuminated that the welder, even with the helmet lifted, cannot see the welding joint without an additional light source. This situation can lead to poor quality welds if the welder proceeds with poor vision, as well as lead to significant delays in securing proper illumination. Hence the need for a convenient illumination source, located to illuminate the welder's field of view. A solution is to fit the light source onto the welding helmet by an attachment mechanism.

Attaching a lighting source such as a strip of light emitting diodes (LEDs) to a surface of a helmet leaves the lighting source exposed to heat, dust, metal particles, and welding spatter of the welding environment. For example, if the light source extends from the surface of the welding helmet, welding spatter can get caught in a lip and/or groove at the interface of the two and create a fire hazard, as the molten metal will burn through most materials. The present attachments and helmets provides a solution for additional lighting that is safe, efficient, easily replaceable, and durable, providing significant benefits over conventional systems.

FIG. 1 illustrates an example welding helmet 100 including a lens retaining bezel 104 having one or more channels 108, 110, 112 and 114. Each of the channels 108-114 are configured to accept one or more light sources, such as a light emitting diode (LED), organic light emitting diodes (OLEDs), or any other type of light source configured to fit in the bezel 104. As shown, channels 108 and 114 are located at the top and bottom of a lens 106, whereas channels 110 and 112 are located at the sides of the lens 106. The light source(s) can be a strip of LED lights or other type of lighting designed to fit into the channels 108-114 (see, e.g., FIGS. 5-7). The light source(s) and/or separate channels can be secured by one or more attachment mechanisms (see, e.g., FIGS. 8 and 9).

The light(s) can be configured on the helmet 100 as one or more lights shining forward (e.g., in the direction of viewing of the wearer of the helmet) and/or in other directions to provide illumination. The number and/or orientation of the lights may be different for different forms and/or uses of helmets, including welding-type helmets. The light(s) may be arranged to create any desired illumination pattern and/or may be user-adjustable to change the illumination patterns, based on the work performed, environment, tools in use, and/or preference of the operator.

In some examples, the helmet 100 also includes a covering 102 to which the bezel 104 may also attach. Additionally or alternatively, a piece separate from the bezel 104 can be secured to the covering 102, configured to attach the light source(s) to the helmet 100 at a location other than the bezel 104. This can allow for additional lighting, as well as alternative lighting direction.

In an example, the helmet 100 further includes one or more sensors (not shown), such as a photodiode, to activate the light source in response to light intensities as viewed by the operator. The LED light strips can be turned on and off by an external sensor input configured to detect the presence of welding arc for power management. Sensor types generally include light sensors, but can also include sensors configured to detect the electromagnetic field of the arc. The LED lights strips can have a control adjustment to modify brightness or change color.

Figure 2:
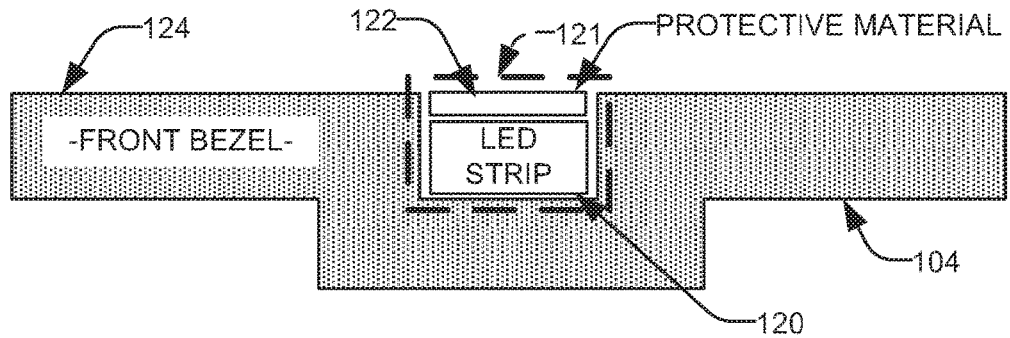
FIGS. 2-4 illustrate example channel configurations for attachment of light source(s), in accordance with aspects of this disclosure.
Figure 3:
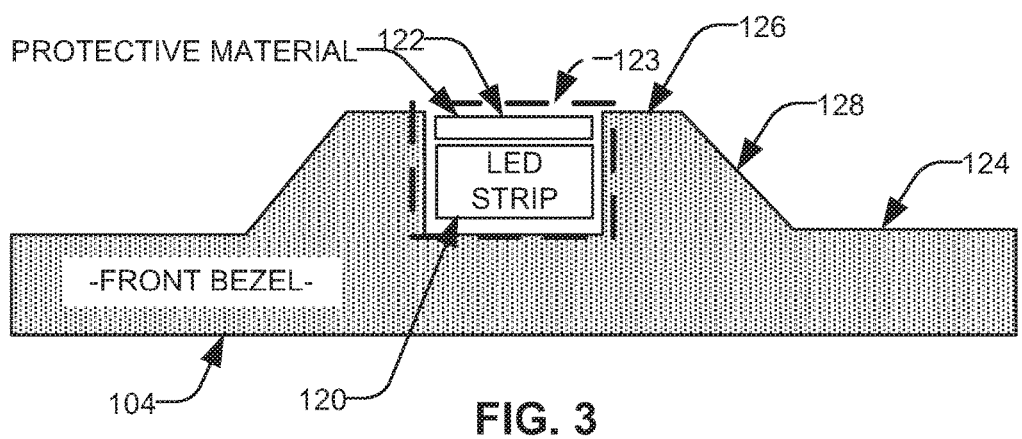
Figure 4:
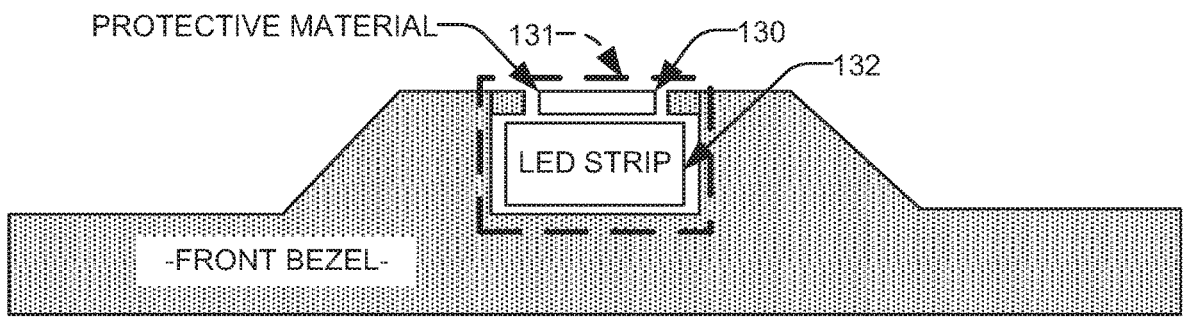

In disclosed examples, the channels 108-114 are recessed such that a surface of the light source(s) and/or the protective cover is flush with the external surface of the bezel 104 (see, e.g., FIGS. 2-4). Attaching the light source into a recessed channel provides significant advantages over attachment to a flat surface on the helmet 100. The helmet 100 may have few flat surfaces, and that limits the location to which the light source(s) can be attached and limits the field of illumination, which may not correspond to the field of vision of the welder depending as head position changes and environmental objects enter and potentially obscure the welder's field of view. Additionally, attaching bulky equipment to the helmet to enhance lighting, such as a flashlight, can prevent moving the helmet into tight spaces.

In some instances, light sources attached to a flat surface, for example, at or below the lens 106 will obstruct the lower portion of the user's field of view. An effective and versatile light configuration will place the light source(s) as close to the welder's eyes as possible and surrounding the lens 106 in order to generate a more dispersed light pattern than a focused beam from a single source (e.g., a flashlight).

Moreover, the placement of the light sources can vary within and between channels, and adjusted by welders to suit the task at hand. In some examples, a helmet could have a plurality of channels and the welder can remove a light source from one channel and place it into another depending on their preference.

As welding requires the welder to change position, lighting configurations should be customizable such that a welder can place the light source in a desired configuration. A beneficial example placement for a light source is a placement that provides the greatest illumination per unit of electrical power for the particular application. When considering placement of the light source(s) on the helmet 100, caution should be exercised in fixing the light source to the welding lens itself. If the light source(s) are close to the welder's eyes, a glare can be created on the polycarbonate cover that may be placed in front of the welding lens. Advantageously, a welder can add and/or modify the position and amount of lighting as needed and at the work site.

FIGS. 2-4 illustrate examples of configurations of a channel 121 for attachment of lighting to a bezel 104. The front bezel 104 can be of any shape, and can be attached to the helmet 100 using a variety of mechanical attachments (see, e.g., FIGS. 5-9). Providing a groove/channel 121 on the front surface 124 of the bezel 104 allows for the light source 120 to sit recessed within. The channel 121 provides a flat surface 124 for attaching the light source 120 and allows the light source 120 to sit flush relative to the front surface 124 of the bezel 104, eliminating ledges and/or lips that could be a safety hazard to welding spatter. The channel 121 can be of any width and depth suitable to house the light source 120. In some examples, the dimensions of the channel 121 match the width of the light source 120 for a press fit. The depth of the channel 121 can be selected such that the outer surface 124 of the bezel 104 can sit higher than the light source 120 placed in the channel 121. This allows for a protective cover 122 to be placed over the light source 120, with the final assembly having the outer bezel surface 124 sitting flush with the protective cover 122 to eliminate ledges.

As shown in FIG. 2, the bezel 104 can include a recessed channel 121 of a size to accept a light source 120. In the example of FIG. 2, the channel 121 is configured such that the light source 102 fits completely within the channel 121, such that a protective material 122 can be placed in a space above the light source 120 within the channel 121. As shown, when in place the protective cover 122 is made flush with a surface 124 of the bezel 104, which eliminates grooves on the surface of the bezel 104 such that spatter does not buildup during welding.

The protective cover 122 can be made of a clear plastic material to protect the light source 120 from sparks, spatter, dust, and/or smoke that can permanently damage the light source 120. Advantageously, in accordance with the configuration described in FIGS. 1-3, the clear plastic material can be replaced periodically. Additionally or alternatively, a translucent silicone cover can be used to protect the light source 120.

A silicone protective cover can be replaced by a protective material designed to function as an optical filter to modify the color of the light from the LED strips. The groove can be designed such that instead of using an additional protective element to cover the LED strips, the clear polycarbonate lens cover used to protect the auto-darkening lens can slide over the LED strip eliminating the needs for an additional clear protective element to cover the LED strip in the groove.

FIG. 3 illustrates another example bezel 104, where wall(s) 126 extend from the bezel surface 124. In this example, material on the surface 124 of the bezel 104 can be extruded to create a channel 123 as shown in the FIGS. 3 and 4. With the raised channel 123, the walls 126 will be tapered toward the outer surface 124 of the front bezel 104, to eliminate ledges and provide a path for the spatter to slide off. The walls 126 create a channel 123 raised up from the bezel surface 124 such that the light source 120 can be completely enclosed within the channel 123. The walls 126 are defined by a sloped surface 128 to ensure spatter does not collect in corners and/or grooves on the bezel surface 124.

FIG. 4 illustrates yet another example bezel 104. As shown, the channel 131 includes an area 132 dimensioned to house the light strip, similar to the channel shown in FIGS. 2 and 3. The channel area 132, however, is configured with a lip 130 extending inward. This creates a blocking mechanism such that a light source 120 within the bezel 104 cannot be accidentally or easily removed. Thus, the protective material 122 is dimensioned differently than the light source 120 to fit between the sides of the lip 130.

Figure 5:
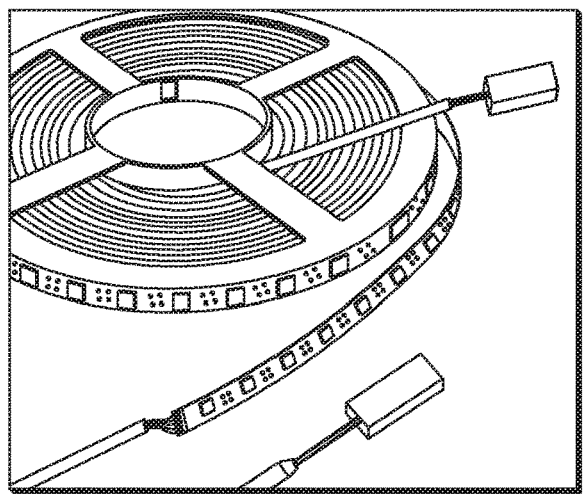
FIGS. 5-7 illustrate examples of lighting, protective covering for the light source(s), and attachment mechanism for the lighting, in accordance with aspects of this disclosure.
Figure 6:
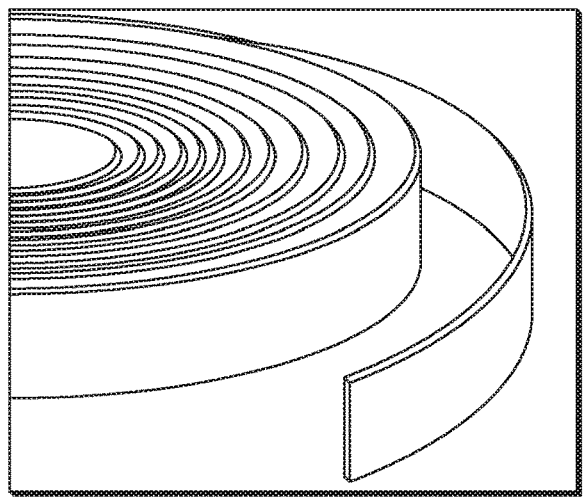
Figure 7:
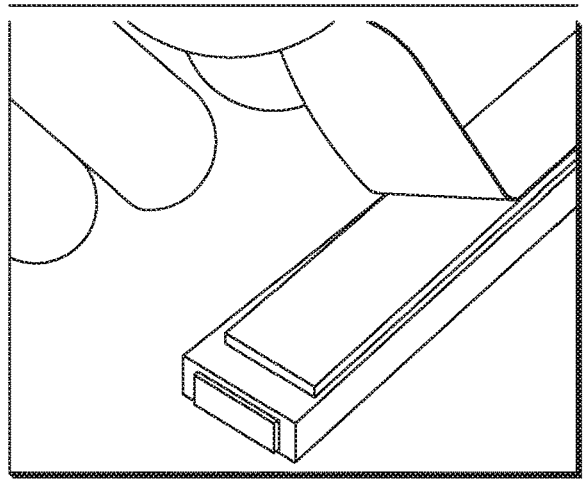

FIGS. 5-7 illustrate examples of light source(s), protective covering for the light source(s), and attachment mechanisms for the light source(s), in accordance with aspects of this disclosure.

FIG. 5 is an example of a light source, such as a tape with embedded LEDs. The LEDs can be placed within a channel and covered with a protective covering, as described with respect to FIGS. 1-4. In another example, the light source can be encased in a protective cover, such as the cover shown in FIG. 6, and then inserted into the channel. In some examples, the protective cover can be attached to the bezel mechanically, and/or with an adhesive, such as an adhesive tape shown in FIG. 7. The protective cover can be made of a rigid or flexible material. In some examples, the protective cover is made of a deformable material, such that once formed in a particular shape the protective cover can substantially maintain the chosen form. In some examples, the light source can be modular, such that multiple light strips can be connected together. In examples with a flexible protective cover and light source, the channel and/or attachment mechanism can be configured to conform the shape of the light source and protective cover to the contour of the bezel and/or surface of the helmet.

The LED strip can be adhered using a variety of methods including mechanical attachments secured to or built into the bezel itself (e.g., a press fit channel), adhesives, Velcro, etc. The LED strip can be secured to the front bezel with a LED strip installed from the manufacturer for easy replacement. The elimination of the need for a user to manually attach the light source is desirable as improper placement can compromise the function and durability of the light assembly if not attached properly.

Also the disclosed helmet and attachment mechanisms reduces costs as there is a cost to having welders in a manufacturing setting spend time attaching light source(s) to a welding helmet. From a replacement standpoint it also keeps the cost down as the welder can quickly detach a worn out bezel and replace it with a new one that includes a light source. Replacing a component part versus the entire shell of the welding helmet also saves part cost, as it uses less material, has a simpler geometry to manufacture, and is smaller/lighter to ship. The time to replace an entire helmet shell with the LEDs adhered thereto is also significantly longer than replacing only the front bezel.

FIG. 8 illustrates examples of lighting attachment mechanisms for the lighting source, such as clip-in attachments with adhesive tape on one side for attachment to the helmet and/or bezel. FIG. 9 shows an example clip being positioned on a helmet frame below the field of view of one wearing the helmet (see also FIGS. 16-19).

Figure 10:
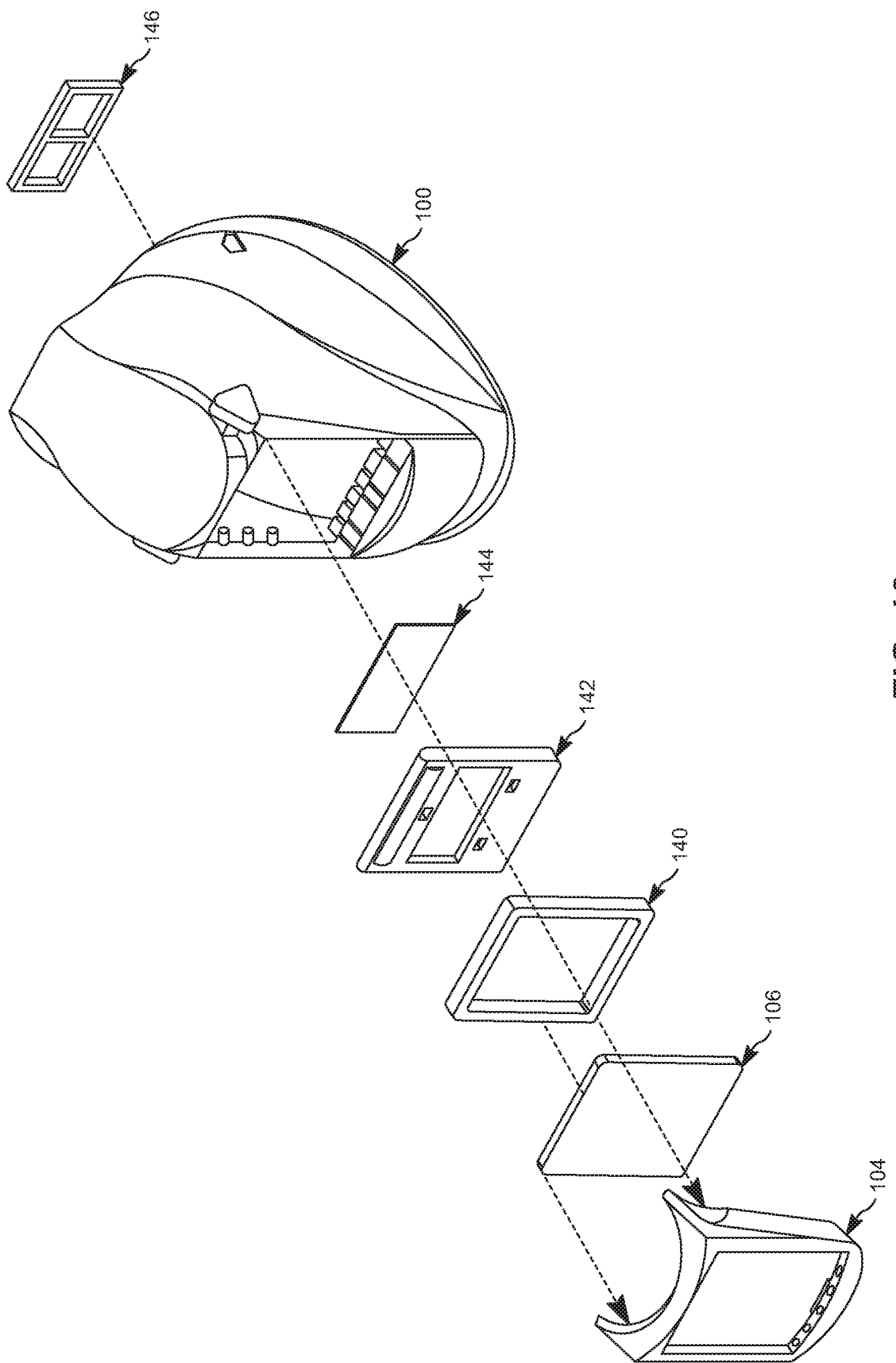
FIG. 10 illustrates an exploded view of an example helmet with one or more protective covers and/or lenses, in accordance with aspects of this disclosure.

FIG. 10 illustrates an exploded view of an example helmet 100 with one or more protective covers and/or lenses. In the example of FIG. 10, a front bezel 104 can be attached to a lens 106, which can then be secured to the helmet 100. One or more lenses and/or filters 140, 142, 144 can also be used. These can include protective layers, auto-darkening filters, a display screen to provide computer enhanced visuals (e.g., augmented reality, information associated with welding tools and/or processes, etc.), as well as other desirable filters, lenses, etc. A lens 146 can be included with the helmet 100 to provide further protection or magnification, as needed for the particular application and/or wearer.

In examples, the front bezel 104 allows welders to easily replace the cover lens 106, which can be a clear plastic consumable that protects the ADF from scratches, dust, smoke etc. This front bezel 104 is a suitable location for integration of the light source 120, as it would serve to illuminate a good portion of the welder's field of vision. Some multi-purpose welding helmets have an integrated grinding shield such that when a visor containing an ADF lens can be rotated with a clear grind shield underneath. The lighting source also has to be multifunctional such that if the welder lifts the visor, the light source can still illuminate objects in their field of vision when looking through the clear grinding shield.

Figure 11:
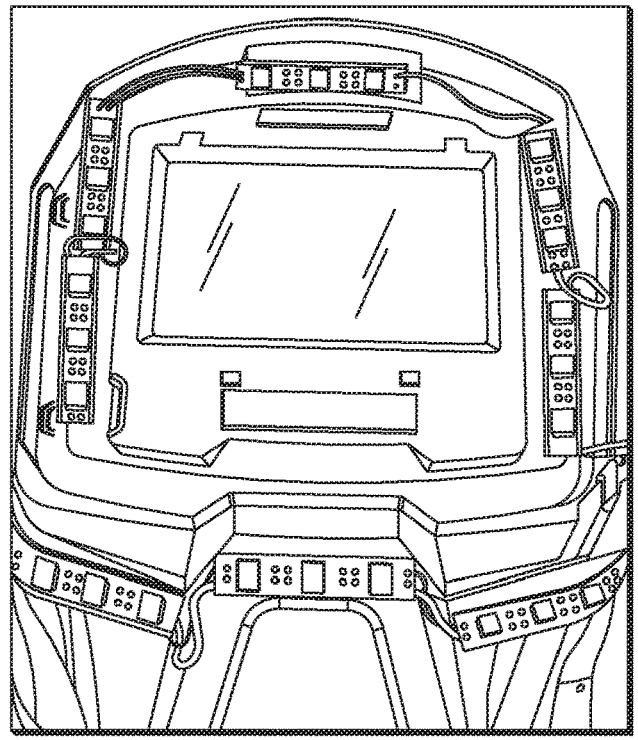
FIGS. 11-19 illustrate examples of helmets with possible light source(s) placement, in accordance with aspects of this disclosure.
Figure 12:
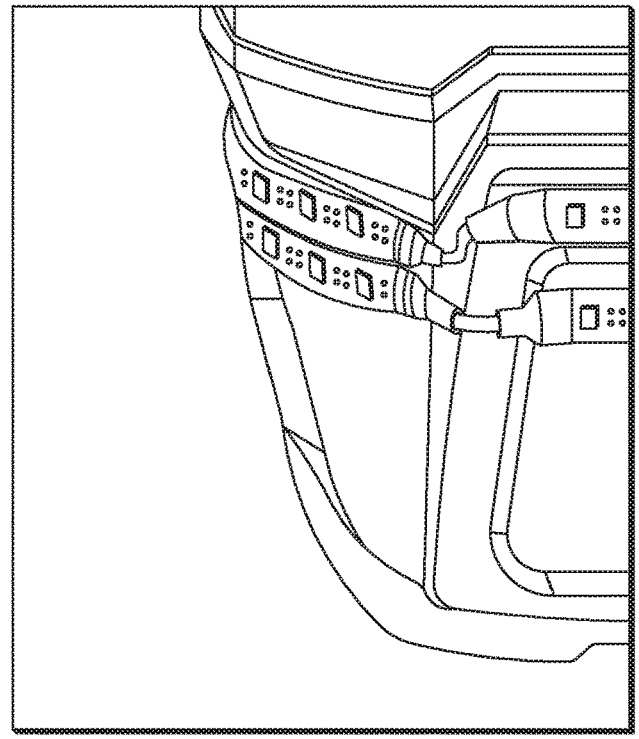

FIGS. 11-14 illustrate examples of possible lighting placement on or around an industrial helmet, in accordance with the examples provided in FIGS. 1-10. In examples, FIGS. 11 and 12 illustrates a welding helmet in which the light source(s) are positioned around the perimeter of the bezel that either shines forward for illumination to the user viewing through the auto-darkening lens, and/or in other directions such as downward so illumination can be beneficial in combination welding and grinding helmets. The directional configuration may allow the operator to, for example, flip up an auto-darkening weld shield portion of the welding helmet to use a clear grind shield portion, while maintaining illumination on the work piece from the angled lights on the flipped up lens retaining bezel.

Figure 13:
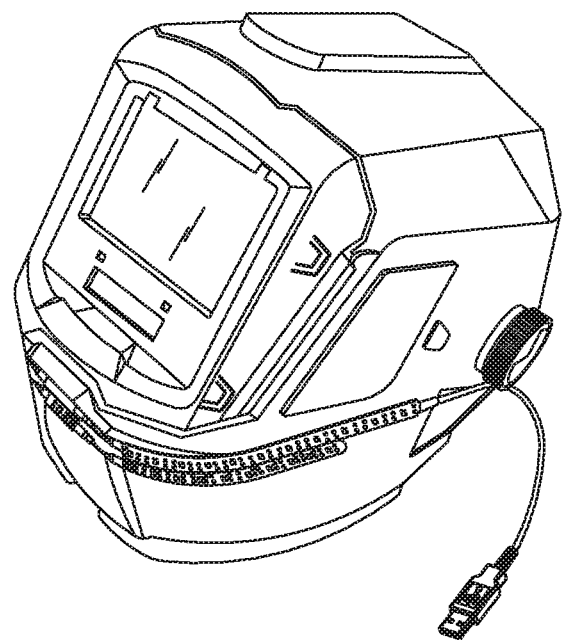
Figure 14:
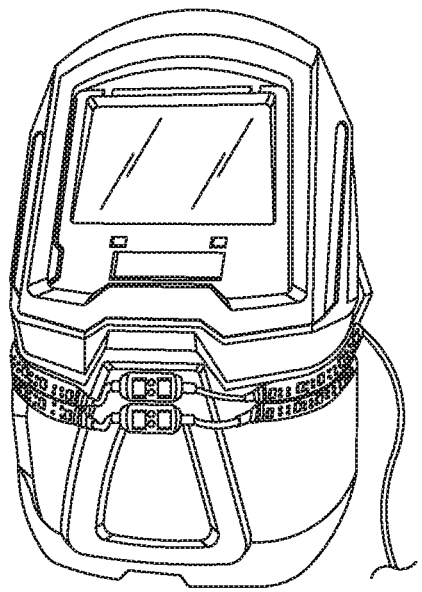
Figure 15:
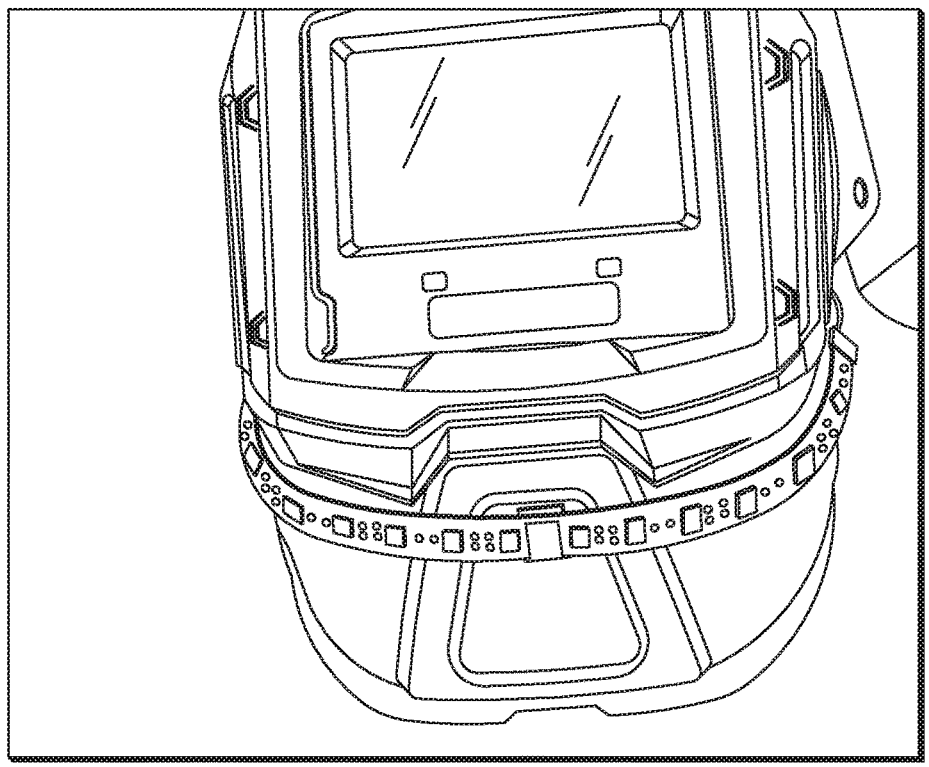
Figure 16:
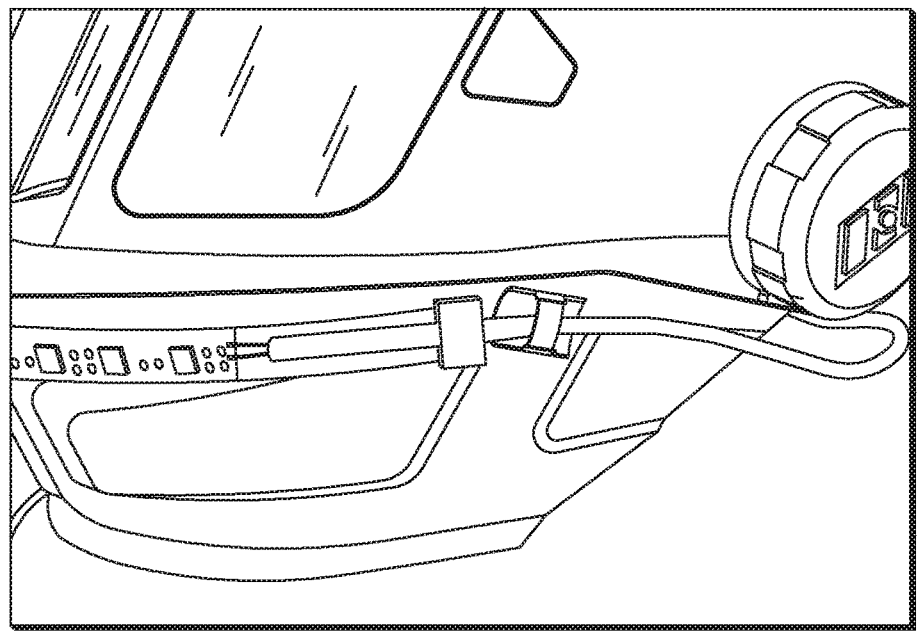
Figure 17:
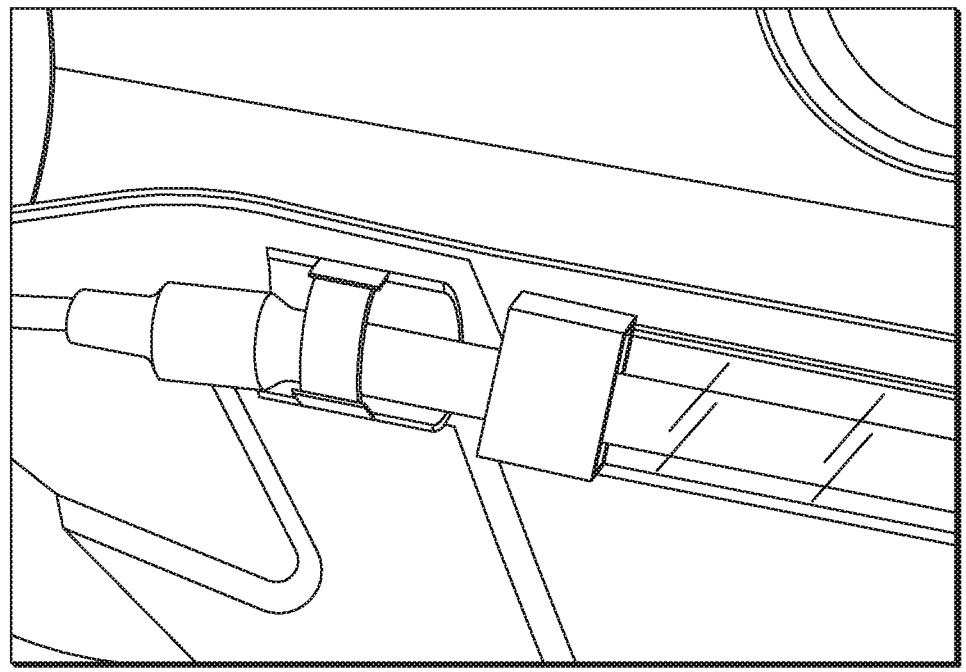

As shown in FIGS. 12-14, the welding helmet may include a cable, integrated power conduit, and/or any other conductor from the light sources on the bezel to a power source to provide power for the light source. Example power sources include batteries, solar cells, and/or any other power source, which may be dedicated to powering the lights or may be shared with other circuitry. The cable could be run outside of a shell of the welding helmet and/or through an internal designated path incorporated into the helmet. The power source may also be integrated into the bezel and/or the helmet. In some examples, the bezel includes light sensors that disable the light(s) while welding by detecting the light from the welding arc to conserve power.

Figure 18A:
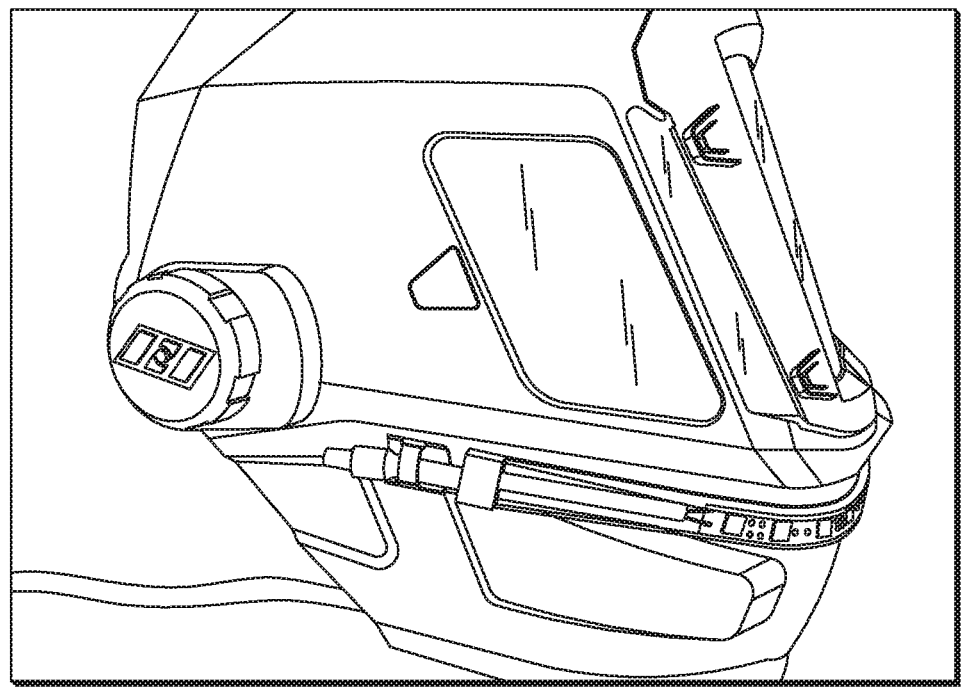
Figure 18B:
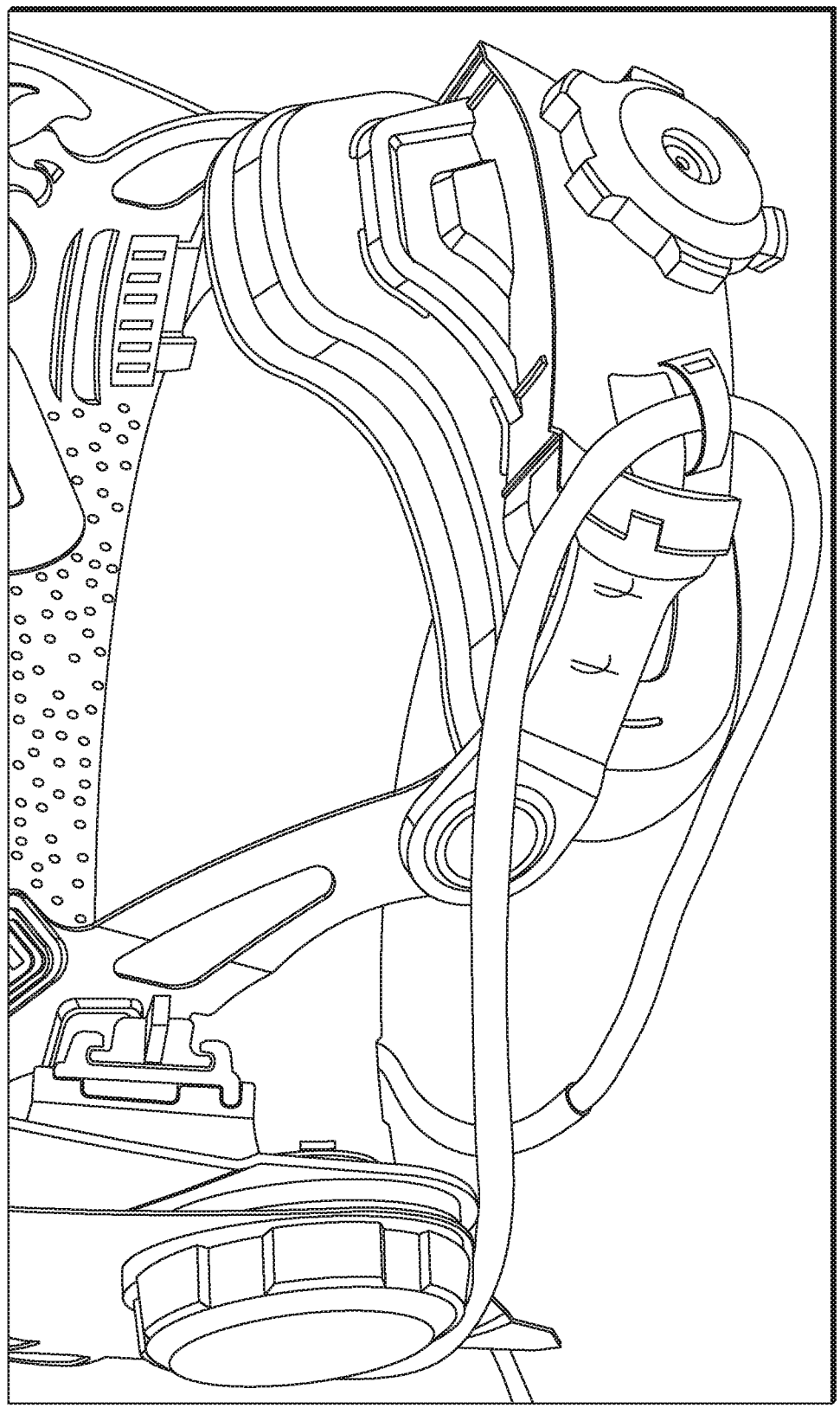
Figure 19:
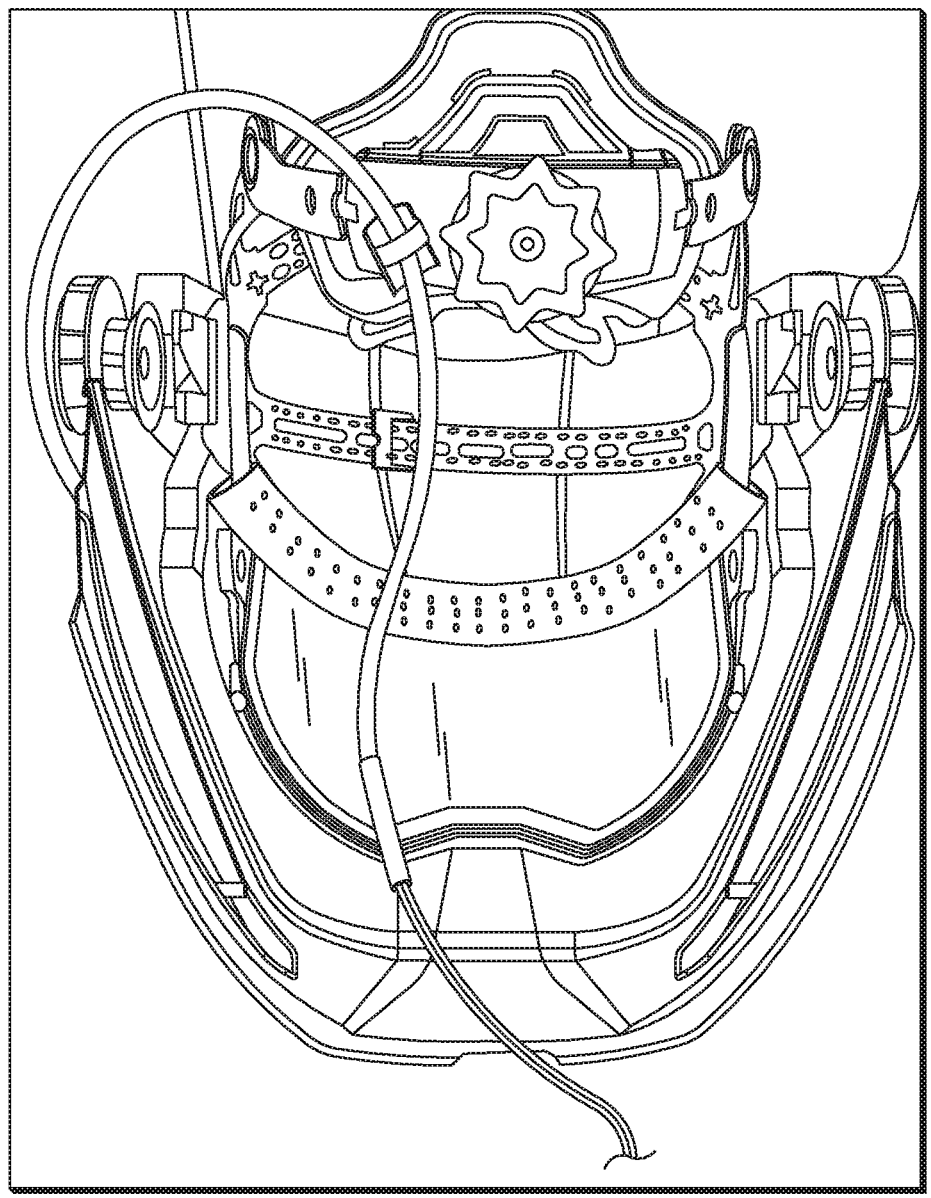
Figure 20:
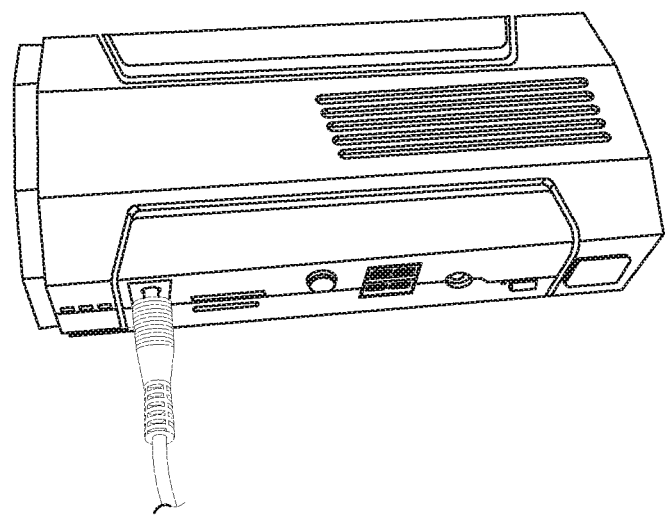
FIG. 20 illustrates an example power source, in accordance with aspects of this disclosure.

As shown in FIGS. 15-18, the light source can be within a tube or casing and secured to the helmet. In the example of FIGS. 15-18, one or more clips can be used to secure the light source and/or the cabling to the helmet to ensure little or no slack is found in the cabling. FIGS. 18 and 19 illustrate the cabling at the rear of the helmet. The cable can be fixed at one or more locations at the rear of the frame such as to direct the cabling away from the welding operation. The cabling can connect with a battery pack, such as shown in FIG. 20, which can be secured to a belt of the welder.

In some examples, light source 120 can be powered by a battery that can provide power for the LEDs to last throughout an entire work shift (e.g., 8-12 hours). The battery may be integrated with the helmet itself. Additionally or alternatively, due to the size and weight of the required battery, the battery can be worn on the user remote from the helmet 100, such as in a pocket or around the waist, connected through a power cable (see, e.g., FIGS. 13-19). This will mitigate the discomfort associated with carrying a heavy battery source. The power cables can be covered in a protective cover and/or tubing to prevent damage. For example, respiratory welding helmets use a belt mounted purifying air blower that is battery powered and can be designed to serve as a power source for the light source. At the end of the light source (e.g., at the back edge of the helmet) a power connector female plug connects the light source to the power cable (e.g., a male receptacle) which then plugs into a battery. The power connector can be any commonly used receptacle such as a USB, coaxial, etc. USB C is desirable particularly due to the widespread availability of USB cell phone chargers and portable chargers.

In examples, the power cable can be routed through the back of the headgear (self-adhesive cable mount attached to back cushion shown below) and down the user's back to protect the cable. This arrangement will prevent welding splatter from getting on the cable, as well as prevent snags. The cable can be held in place by one or more clips to maintain a tight fit against the helmet and/or other equipment, while allowing sufficient slack to accommodate head movement. In some examples, the clip can have an adhesive backing secured to the helmet and/or equipment. If needed, washers or other components, such as a collet or mechanical attachment, can be used to ensure the cable is not subject to snags and/or tugging out of place. In some examples, the light source can be a one foot (1 ft.) LED strip, with approximately 18 LEDs per foot, with a power consumption of approximately 274 maH/ft. This strip would generate approximately 380 lumens/ft. and weigh approximately 40-50 grams. An example battery is a rechargeable lithium ion battery, rated for 12V at 2600 maH (e.g., a maximum 2 A output) or 5V 5160 maH (e.g., a maximum 2 A output), with an approximate size of 6 inches in length an 3 inches wide, with a 1 inch thickness. The battery would therefore be of a size that would fit in a pocket or clip to a welder's belt. In some examples, solar panels on the surface of the welding helmet can be used to supplement or recharge the battery for the LED strips.

Figure 21:
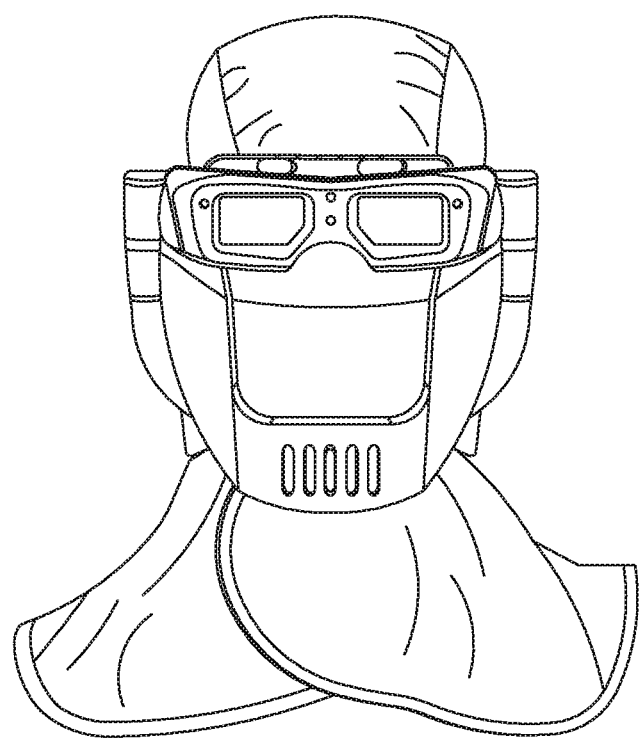
FIG. 21 illustrates another example of protective headgear, in accordance with aspects of this disclosure.

Additionally, as shown in FIG. 21, other types of protective headgear can employ the lighting attachment mechanism described with respect to FIGS. 1-14. In some examples, other types of industrial helmets can include lighting attachments, as well as military and/or police helmets, SCBA, SCUBA, or other headgear. In some examples, a smaller profile protective covering, such as goggles, can accommodate a channel to accept a light source.

The examples described herein provide multiple advantages in the art of illumination in a work and/or industrial setting. The attachment mechanisms and light source(s) result in improved illumination to workpiece for welders improving productivity and quality of welds, while providing a durable and safe solution able to withstand the hazards of the welding environment. The attachment mechanism is easily retrofitted to existing helmets, which allows a user to easily and quickly replace existing, worn out lighting systems with the light source described herein. The design minimizes weight added to the helmet while providing a cost effective, long lasting light source.

As described above, the groove/channel can be created on any surface of a welding helmet, creating a customizable and durable attachment location for a plurality of light sources.

In some examples, a separate component can be molded and/or machined with a groove/channel configured to secure the light source. This independent component could then be coupled to the welding helmet as desired.

In some examples, a single, bright LED light can be used instead of or in addition to a strip of LED lights, such as in applications where a focused light is required compared to a more diffuse lighting that the LED strip provides.

The placement of these LED strip on these grooves is not limited to a traditional welding helmet. It can be applied on any industrial face shield. There are alternate form factors of welding helmets such as welding goggles & glasses that can also have LED lights attached within recessed channels and covered by a protective element. Furthermore, the recesses are ideally located on a component that is easily/quickly replaceable.

In examples, the helmet could combine the auto-darkening lens or a standard passive welding filter with an augmented reality system where the augmented reality system uses at least one camera to map the objects in the surrounding. By having the augmented reality display placed in between the welder's FOV and the arc, it can generate a three-dimensional representation of the work piece allowing the welder to clearly see the workpiece even when the lens is darkened through welding. The representation generated by the display system of the augmented reality. One challenge when welding is the arc is very bright, but the surrounding workpiece is dark. By mapping the objects in the welder's surrounding, and then generating a three-dimensional display while the welding lens is dark, is a method that can overcome some challenges of the welding environment.

As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. For example, block and/or components of disclosed examples may be combined, divided, re-arranged, and/or otherwise modified. Therefore, the present method and/or system are not limited to the particular implementations disclosed. Instead, the present method and/or system will include all implementations falling within the scope of the appended claims, both literally and under the doctrine of equivalents.

What is claimed is:

1. A welding-type helmet comprising:
a lens defining a top, a bottom, a first side, and a second side, wherein the lens is coupled to the helmet and configured to protect a user wearing the helmet; and
a channel recessed from an external surface of the helmet and adjacent to at least one of the top, bottom, first side, or second side of the lens, the channel being externally accessible from the helmet and configured to receive and house a removable light source that is surrounded on three sides by the channel,
wherein a space is formed within the channel between: 1) a surface of the light source, and 2) a plane corresponding to the external surface of the helmet, when the light source is housed within the channel.

2. The helmet as defined in claim 1, further comprising a protective cover configured to fit within the space such that an exterior surface of the protective cover is substantially flush with the external surface of the helmet, wherein the protective cover comprises a translucent silicon material or a translucent polymer material.

3. A bezel for an industrial helmet comprising:
a channel with two internal side walls and an internal surface configured to house a removable light source in contact with the internal surface of the channel within the channel; and
a protective cover configured to fit within a space within the channel such that an exterior surface of the protective cover is flush with an outermost surface of the two internal side walls, wherein an external surface of the bezel slopes upward to the outermost surface of each internal side wall at an angle with respect to the external surface of the bezel.

4. The bezel as defined in claim 3, wherein the two internal side walls extend from the external surface of the bezel such that the internal surface of the channel is coplanar with the external surface of the bezel.

5. The bezel as defined in claim 4, wherein, when the light source is housed in the channel, the two internal side walls extending beyond the light source to create the space within the channel.

6. The bezel as defined in claim 3, wherein the bezel is configured to removably attach to a welding-type helmet, the light source being configured to connect with a power source remotely located from the helmet.

7. The bezel as defined in claim 3, further comprising a battery to power the light source, the battery secured to the helmet as a removable battery pack by a frame configured to secure a clip and the battery pack at a rear portion of the frame.

8. A welding-type helmet comprising:
a bezel configured to removably attach to the helmet, the bezel including a channel recessed from an external surface of the bezel, wherein a space is formed within the channel between: 1) a surface of a light source, and 2) a plane corresponding to the external surface of the bezel when the light source is housed within the channel; and
a protective cover comprising a translucent material configured to fit within the space such that an exterior surface of the protective cover is substantially flush with the external surface of the bezel.

9. The bezel as defined in claim 3, wherein the bezel is configured to removably attach to a surface of a welding-type helmet, the bezel arranged between the welding-type helmet and the light source.

* * * * *